(12) United States Patent
Cohen et al.

(10) Patent No.: US 7,214,371 B1
(45) Date of Patent: May 8, 2007

(54) TISSUE ENGINEERED BIOGRAFTS FOR REPAIR OF DAMAGED MYOCARDIUM

(75) Inventors: Smadar Cohen, Beer Sheva (IL); Ayelet Dar, Rehovot (IL); Sharon Etzion, Beer Shevea (IL); Anat Perets, Bet-Shemesh (IL); Sigalit Shaprut, Beer Sheva (IL); Jonathan Leor, Gane' Tikva (IL)

(73) Assignee: Ben-Gurion University of the Negev Research & Development Authority, Beer-Sheva (IL)

( * ) Notice: Subject to any disclaimer, the term of this patent is extended or adjusted under 35 U.S.C. 154(b) by 0 days.

(21) Appl. No.: 09/654,276

(22) Filed: Sep. 1, 2000

(51) Int. Cl.
*C12N 5/08* (2006.01)
*A61K 9/14* (2006.01)

(52) U.S. Cl. .................... 424/93.7; 424/93.1; 424/489; 424/484; 424/488; 435/325; 435/366

(58) Field of Classification Search ............. 424/93.21, 424/489, 93.7, 93.1, 488, 484; 435/455, 435/325, 378, 366
See application file for complete search history.

(56) References Cited

U.S. PATENT DOCUMENTS

| 5,494,682 A | * | 2/1996 | Cohen et al. ................ 424/489 |
| 6,099,832 A | * | 8/2000 | Mickle et al. ............ 424/93.21 |

FOREIGN PATENT DOCUMENTS

| WO | 97/44070 | 11/1997 |
| WO | WO 97/44070 | * 11/1997 |
| WO | 99/03973 | 1/1999 |
| WO | WO 99/03973 | * 1/1999 |
| WO | 99/65463 | 12/1999 |

OTHER PUBLICATIONS

Kaufmann et al., Xenotransplantation, 1995, Annu. Rev. Immunol., vol. 13, pp. 339-367.*
Leor et al., Abstracts selected for the presentation at the XXIst Congress of the European Society of Cardiology, Aug. 28-Sep. 1, 1999, Barcelona Spain, 1999, European Heart Journal, vol. 20, Abstract.*
Li et al., Survival and function of bioengineered cardiac grafts, 1999, Circulation, vol. 100(suppl. II) II-63-II-69.*
Cohen, et al., "Controlled Delivery Systems For Proteins Based On Poly (Lactic/Glycolic Acid) Microspheres" *Pharmaceutical Research*, vol. 8, No. 6, pp. 713-720, 1991.
Kanter, et al., "Distinct Patterns of Connexin Expression In Canine Purkinje Fibers And Ventricular Muscle"*Circ. res.*, vol. 72, No. 5, May 1993.
Leor, et al., "Transplantation of Fetal Myocardial Tissue Into The Infracted Myocardium Of Rat" *Circulation 94*, Suppl, II, pp. 332-336, Nov. 1996.
Li, et al., "Survival And Function Of Bioengineereed Cardiac Grafts"*Circulation 19*, pp. 1163-1169, Nov. 1999.
Shapiro & Cohen, "Novel Alginate Sponges For Cell Culture and Transplantation" *Biomaterials*, vol. 18, No. 8, pp. 583-590, 1997.
Taylor, et al., "Regenerating Functional Myocardium: Improved Performance After Skeletal Myoblast Transplantation"*Nature Medicine*, vol. 4, No. 8, pp. 929-933, Aug. 1998.
Horrigan et al., 1996, *Circulation*, 94(8):1927-1933 "Coronary Heart Disease/Myocardial Infarction: Reduction in Myocardial Infarct Size by Basic Fibroblast Growth Factor After Temporary Coronary Occlusion in a Canine Model".
Itskovitz-Eldor et al., 2000, *Molecular Medicine*, 6(2):88-95 "Differentiation of Human Embryonic Stem Cells into Embryoid Bodies Comprising the Three Embryonic Germ Layers".
Rowley et al., 1999, *Biomaterials*, 20:45-53 "Alginate hydrogels as synthetic extracellular matrix material".
Thomson et al., 1998, *Science*, 282:1145-1147 "Embryonic Stem Cell Lines Derived from Human Blastocysts".
Tomita et al., 1999, *Circulation*, 100(Suppl. II):II-247-II-256 "Autollogous Transplantation of Bone Marrow Cells Improves Damaged Heart Function".
Wobus et al., 1991, *Differentiation*, 48:173-182 "Pluripotent mouse embryonic stem cells are able to differentiate into cardiomyocytes expressing chronotropic responses to adrenergic and cholinergic agents and $Ca^{2+}$ channel blockers".
Superdock et al., 1993, *Seminars in Respiratory Infections*, 8(3):152-159 "Immunosuppressive Drugs and Their Effects".
Woodley et al., 1990, *Cardiology Clinics*, 8(1):83-96 "Immunosuppression Following Cardiac Transplantation".
Li et al., 1999, *Circulation*, 100(supp. II):II-63-II-69 "Survival and Function of Bioengineered Cardiac Grafts."

* cited by examiner

*Primary Examiner*—Anne M. Wehbe'
(74) *Attorney, Agent, or Firm*—Merchant & Gould P.C.

(57) ABSTRACT

The invention is directed to tissue-engineered biografts, methods for preparing the biografts of the invention, and methods for repairing a damaged myocardium in a mammal. The methods of the invention can include providing a three-dimensional porous polysaccharide matrix; introducing mammalian cells into said matrix; growing said cells in said matrix in vitro, until a tissue-engineered biograft is formed; and transplanting the tissue-engineered biograft onto myocardial tissue or myocardial scar tissue of said mammal. The tissue-engineered biograft of the invention can form a contracting tissue. The methods of the invention can optionally include removing scar tissue or dead tissue from the site of implantation prior to transplanting the biograft.

9 Claims, 14 Drawing Sheets

TISSUE ENGINEERED BIOGRAFTS FOR REPAIR OF DAMAGED MYOCARDIUM

FIELD OF THE INVENTION

The present invention relates to the use of tissue-engineered cardiac biografts for transplantation into damaged myocardium.

BACKGROUND OF THE INVENTION

Despite recent advances in the treatment of acute myocardial infarction (MI), attempts to repair extensive myocardial damage and to treat heart failure are often met with limited success. One of the reasons for the lack of success is that the myocardium is unable to regenerate because cardiomyocytes do not have the capacity for replication after injury, and furthermore because there are apparently no muscle stem cells in the myocardium.

Existing strategies for restoring heart function after myocardial injury are practically limited to cardiac transplantation. Since the supply of donor hearts is limited, tissue engineering appears to be a promising approach for the formation of new functional tissue to replace lost or failing tissue. Earlier studies indicated the possibility of transplanting isolated cardiomyocytes or myoblasts in order to enhance cardiac function following myocardial injury (Taylor et al., Nat. Med., 4:929–33, 1998). However, this approach does not permit the formation of tissue-engineered cardiac biografts having the desired shape, size and consistency.

A bioengineered cardiac graft using fetal myocardial cells contained within a gelatin mesh was recently disclosed (Li et al., Circulation 19, 63–69, 1999). When transplanted into rodent post-infarction myocardial tissue, however, no improvement in cardiac function could be observed. A similar method for producing a myocardial graft in a mammal using scaffolding is disclosed in U.S. Pat. No. 6,099,832. In said patent, cardiomyocytes were either directly introduced into a cryo-damaged myocardial tissue, or were first suspended on scaffolding polymers prior to transplantation. In both cases, the biograft did not provide tissue characteristics such as cell—cell interactions and the formation of extracellular matrix. In addition, the methods of U.S. Pat. No. 6,099,832 do not provide the ability to determine the composition and consistency of the biograft.

In WO 99/03973, mesenchymal stem cells were supported onto a semi-solid or solid matrix, such as collagen and its derivatives, polylactic acid or polyglycolic acid, and rapidly injected into the tissue. However, cells were not implanted within a scaffolding-type matrix prior to transplantation, and therefore there was no creation of tissue-engineered cardiac biograft prior to transplantation.

In WO 97/44070 of the same applicants hereof, the specification of which is incorporated herein by reference, a new method for the preparation of three-dimensional, porous, biodegradable sponges made from polysaccharides is disclosed.

In WO 99/65463 of the same applicants hereof, the specification of which is incorporated herein by reference, a device for the delivery of drugs to mucosal or luminal surfaces using a porous matrix is disclosed. According to a preferred embodiment of said delivery device, the porous matrix comprises an alginate scaffold. However, said porous matrix was used only for mucosal drug delivery.

It has now been surprisingly found, and this is an object of the present invention, that cultured mammalian cells may be grown in vitro in porous three-dimensional alginate scaffolds, leading to the formation of tissue-engineered biografts, said biografts possessing the characteristics of myocardial tissue, including the formation of cell—cell interactions, contractility and extracellular matrix components. Said tissue-engineered biografts may be used for repairing damaged myocardial tissue by transplanting them onto said myocardial tissue.

It is a purpose of the present invention to provide a tissue-engineered cardiac biograft system for use in replacing the scar tissue that is formed following myocardial infarction.

It is a further object of the invention to provide a tissue-engineered cardiac biograft system that is useful for improving impaired cardiac functions following myocardial infarction.

Other objects and advantages of the invention will become apparent as the description proceeds.

SUMMARY OF THE INVENTION

The present invention, as opposed to procedures in which cells are transplanted, enables a control of the tissue formation process prior to transplantation. It is possible to control and determine the shape and size of the graft, the consistency and composition of the graft (e.g. the total number of cells and cell to cell ratio in co-cultures), and its function prior to transplantation. In addition, the scaffold of the present invention is composed of polysaccharides and has a sponge-like morphology as opposed to previous scaffolds which are based on gelatin and are in a configuration of a mesh.

As said, the invention is primarily directed to the use of 3-D porous polysaccharide scaffold in the preparation of tissue-engineered biograft for the transplantation of mammalian cells into the heart, for the purposes of repairing damaged myocardium. Polysaccharide scaffolds useful in the present invention maybe, e.g., those described in WO 97/44070.

Preferably, tissue-engineered cardiac biografts is constructed from mammalian cells that are selected from the group consisting of fetal cardiac cells, neonatal cardiac cells, fibroblasts, smooth muscle cells, endothelial cells, skeletal myoblasts, mesenchymal stem cells and embryonic stem cells.

In another aspect, the invention is directed to a tissue-engineered biograft for transplantation into myocardial tissue or myocardial scar tissue, comprising a porous alginate matrix containing mammalian cells, wherein said cells are cultured in said matrix in vitro prior to transplantation.

The invention further provides a method for repairing a damaged myocardium in a mammal in need of such repair, said method comprising the steps of:
a) providing a three-dimensional porous polysaccharide matrix;
b) introducing mammalian cells into said matrix;
c) growing said cells in said matrix in vitro, until a tissue-engineered biograft is formed, comprising a contracting tissue; and
d) transplanting the tissue-engineered biograft into the myocardial tissue or myocardial scar tissue of said mammal, optionally removing scar or dead tissue from the site of implantation.

In a preferred embodiment of the present invention, a porous alginate matrix is used as a polysaccharide scaffolds.

The tissue-engineered biografts of the present invention present a number of novel features, some of which will be illustrated in the following description and Examples. One such relevant feature is the formation of a contracting cardiac-like tissue, characterized by cell—cell interactions and extracellular matrix components within the tissue-engineered biograft prior to transplantation. Another important feature is the extensive neovascularization that is observed following implantation of the bioengineered cardiac tissue into the infarcted myocardium. It appears that the high degree of neovascularization contributes to the prolonged survival of the cells in the grafts. A further structural characteristic of the tissue-engineered biograft technique is the integration of the tissue with the surrounding myocardial tissue following transplantation. This integration is seen both in terms of the formation of intercellular junctions and tissue ingrowth from the host into the biograft. Furthermore, when the cells used are fetal cardiomyocytes, it is possible to observe differentiation of said fetal cells into mature cardiomyocytes, together with their organization into bundles of myofibers. As a result of all these integration processes, re-modeling of the damaged myocardium can take place. Such re-modeling, in turn, causes an improvement in cardiac function, as witnessed by the attenuation of ventricular dilation and the cessation of further deterioration in contractility and critical pressure/flow parameters that would otherwise occur as part of the normal response to the myocardial lesion.

Many of the advantageous features of the tissue-engineered biograft of the present invention are attributable to the use of polysaccharides such as alginate matrices as scaffolds for the seeded cells. The scaffolds are hydrophilic in nature, which permits their rapid wetting by aqueous media and efficient cell seeding. In addition, as a consequence of the large pore diameter (between 100 and 150 μm), the physical obstruction of liquid flow by the tortuous pore pathway is minimal, allowing relatively free movement of cells into the scaffold pores, with their subsequent uniform distribution throughout the scaffold volume. These matrices display a highly-porous structure, characterized by a high degree of pore interconnectivity. The connectivity of the pores in the alginate scaffolds allows the re-organization of the dispersed cardiac cells into multicellular aggregates, with 3-D cell—cell interactions. Furthermore, ECM components that are secreted by the cells contribute to the compaction of the cell aggregates into a tissue-like form. The contractility of the multicellular aggregates indicates that the newly-organized tissue maintains the characteristics of a cardiac tissue.

The ECM components were apparently synthesized by cardiofibroblasts, which constitute, according to cell purity assay, 30% of the seeded cells. It is possible that the secreted ECM components contribute to the establishment of sufficient cell-matrix interactions to maintain cell survival and differentiation. They are also involved in the process of cell aggregation and compaction.

All the above and other characteristics and advantages of the invention will be further understood from the following illustrative and non-limitative examples of preferred embodiments thereof.

BRIEF DESCRIPTION OF THE DRAWINGS

The above and other characteristics and advantages of the invention will be more clearly understood from the detailed description of the preferred embodiments, and from the attached drawings in which.

DETAILED DESCRIPTION OF PREFERRED EMBODIMENTS

Figure 1:
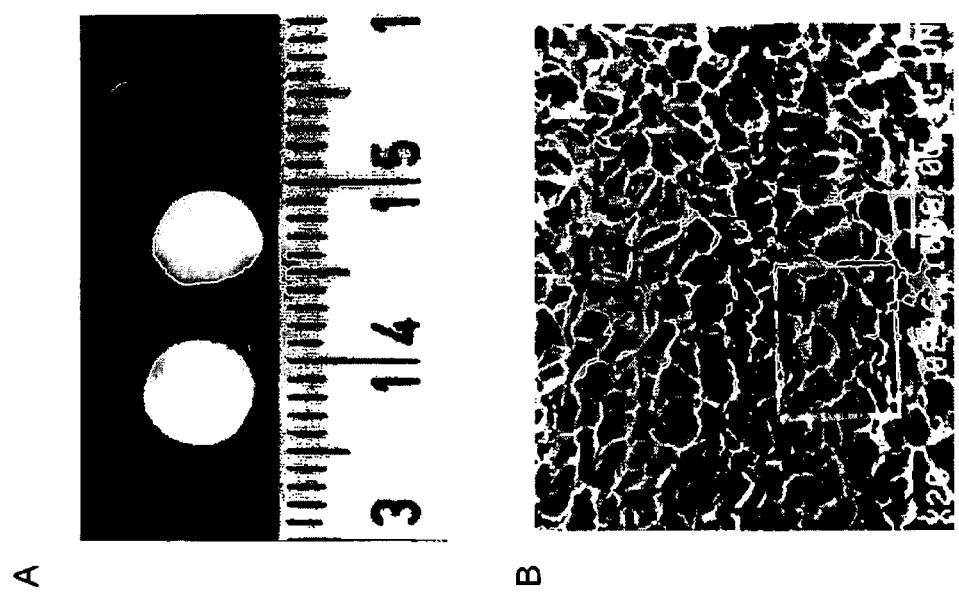
FIGS. 1(A+B) is a photograph of the alginate scaffold used in the study (A) and a scanning electron micrograph of a cross-section of the alginate scaffold (B)

For the purpose of clarity and as an aid in the understanding of the invention, as disclosed and claimed herein, the following terms and abbreviations are defined below:

MI—myocardial infarction

LV—left ventricular

ECM—extracellular matrix

SEM—scanning electron microscopy

VEGF—vascular endothelial growth factor

FACS—fluorescent-activated cell sorter

3-D—3-dimensional b-FGF—basic fibroblast growth factor

G—guluronic acid

In a preferred embodiment of the invention, the fetal cardiomyocytes or neonatal cardiomyocytes are co-cultured with endothelial cells, cardiofibroblasts or smooth muscle cells. In yet another preferred embodiment, said endothelial cells form capillary-like tubes. The advantage of using endothelial cells for capillary formation is that the capillaries formed within the 3-D scaffold form the foundation for its vascularization after implantation. The capillaries provide also signals such as growth factors and extracellular matrix components to attract and enhance blood vessel ingrowth from the host, and to improve the integration of the functional cells. Another advantage is that in vitro capillary formation allows a better control of the capillary distribution inside the scaffold, as opposed to the presently available biografts in which the implantation of scaffolds results in an uncontrollable tissue growth into the scaffolds, which does not leave sufficient space for the functional cells.

According to another preferred embodiment of the invention, the polysaccharide scaffolds further comprise controlled-release polymeric microspheres, said microspheres being able of secreting soluble factors in a controlled manner. In another preferred embodiment, said soluble factors comprise growth factors, genes or DNA. Said microspheres provide a depot for soluble recombinant factors and genes, while controlling their presentation in the diseased tissue or graft. To maximize the effect of growth factors on the seeded cells, the microspheres are incorporated within the alginate scaffolds. The added advantage of using controlled-release microspheres is that, if required, the release pattern of the growth factor from the polymeric microspheres can be adjusted according to specific needs. The microspheres are incorporated into the scaffold during preparation.

Many different mammalian cell types are suitable for use in the method of the present invention. Illustrative and non-limitative examples of suitable cell include fetal cardiomyocytes, neonatal cardiomyocytes, fibroblasts, smooth muscle cells, endothelial cells, skeletal myoblasts, mesenchymal stem cells and embryonic stem cells.

The method of the invention may be applied to the treatment of the myocardial damage that occurs as part of many different diseases and functional disorders. The method, however, is particularly useful when the myocardial damage is due to myocardial infarction. Another example is the treatment of myocardial damage due to a congenital heart defect.

The present invention is further illustrated, but not limited, by the following examples:

EXAMPLE 1

Tissue Engineering of a Cardiac Tissue from Fetal or Neonatal Cardiac Cells within 3-D Alginate Scaffolds Preparation of 3-D Alginate Scaffolds:

The 3-D scaffolds were prepared as previously described (Shapiro and Cohen., Biomaterials, 18 583–90, 1997) from a pharmaceutical-grade alginate, Protanal LF 5/60 (Pronova Biopolymers, Drammen, Norway), which has a G contents (65–75%) and solution viscosity (1% w/v, 25° C.) of 50 cP. Scaffold preparation consists of (i) Preparation of sodium alginate stock solutions, at concentrations of 1–3% (w/v). (ii) Cross-linking of the alginate by adding, dropwise, the bivalent cross-linker, e.g., calcium gluconate. (iii) Freezing the cross-linked alginate and (iv) lyophilization to produce a sponge-like scaffold. The sponges were sterilized using ethylene oxide gas apparatus. The residual ethylene oxide was removed by aeration of the samples with warm air flow. The sponges were stored in laminated bags, at room temperature, until use. A photograph of a typical scaffold is shown in FIG. 1A, and a scanning electron micrograph of the same scaffold is given in FIG. 1B.

Isolation of Fetal and Neonatal Cardiomyocytes:

Fetal cardiomyocytes were isolated as described by Leor et al., Circulation 94, II332–II336, 1996). Briefly, 15-day-old embryos were removed from female rats and their hearts were dissected and placed in a cold dissociation buffer (137 mM NaCl, 5.4 mM KCl, 0.8 mM $MgSO_4$, 5.6 mM Dextrose, 0.4 mM $KH_2PO_4$, 0.3 mM $Na_2HPO_4$, 20 mM HEPES, 500 u/ml penicillin, 100 mg/ml streptomycin, pH 7.5). The ventricles were cut into 1–2 mm cubes, and enzymatically-digested by Trypsin-DNAse. Freed cells were collected in a cold M-199 culture medium, containing 0.5% (v/v) fetal calf serum and 0.002% (w/v) DNAse, centrifuged (0° C., 10 min, 2500 rpm), washed in culture medium and then pre-plated in a 60 mm-dish, for 15–60 min, at 37° C. The nonattached cardiac cells (supernatants) were collected and counted using a Coulter counter. Neonatal ventricular cardiomyocytes were isolated from 2-day-old rats, as described above. The purity of the cells (i.e., percentage cardiomyocytes) was analyzed by Fluorescent-Activated Cell Sorter (FACS) flow cytometry. The cells were permeabilized (15 minutes, 0.5% Triton X-100 in PBS), incubated for 30 minutes in 1% BSA/PBS, and subsequently incubated for 45 minutes with an antibody to sarcomeric tropomyosin (Sigma). After washing with 0.1% Nonidet P40 and 1% BSA/PBS, the cells are incubated with FITC-conjugated goat anti-rat IgG antibody, washed again, and were stained with propidium iodide for DNA contents. The purity of cells was determined Using Epics software.

Culturing of Cardiomyocytes within the 3-D Alginate Scaffolds:

The cardiomyocytes were seeded individually or cocultured with cardiofibroblasts and/or endothelial cells, within the 3-D alginate scaffolds. The cell ratio in the co-cultures varied as desired. The isolated cardiac cells were seeded at a concentration, ranging between $1 \times 10^5 – 2 \times 10^6$ cells/scaffold, within cylindrical alginate scaffolds (5-mm diameter× 1.0 mm-height), placed in a 96-well plate. The cells were seeded onto the 3-D alginate scaffolds, by a dynamic method—the centrifugal packing method. A small volume (50–100 µl) of cell suspension is dropped on top of the scaffold or injected into the center of the device, via a 25 G needle. Immediately after overlayering the cells, the plate containing the scaffolds is centrifuged using a bench-type centrifuge, at 3000 rpm for 5 min. Due to their hydrophilic nature, the alginate scaffolds were easily wetted by the medium, and an efficient cell seeding was achieved. The seeded constructs, supplied with additional 200 µl media, were incubated in a humidified atmosphere of 5% $CO_2$ and 95% air, at 37° C., until characterized (within 24 hours), after which they were transferred to the cultivation bioreactor.

Figure 2:
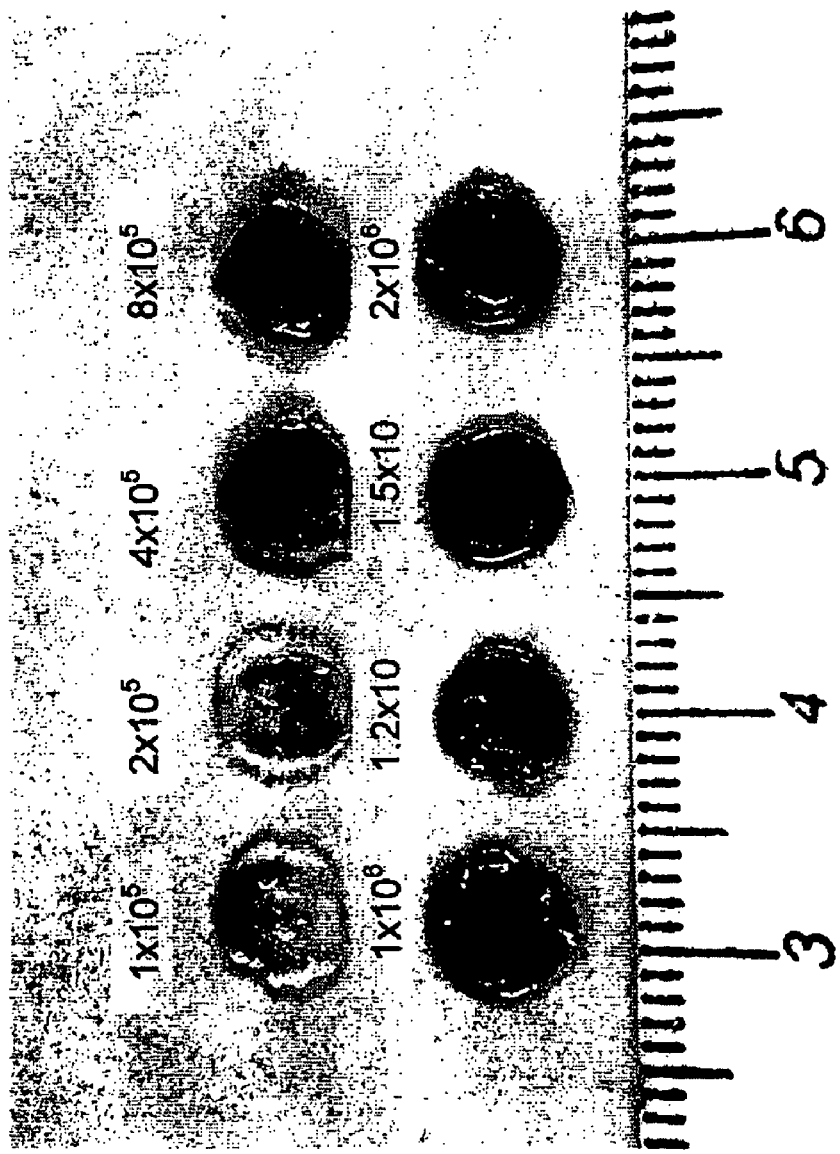
FIG. 2 shows a photograph of the cell-seeded alginate scaffolds as a function of cell seeding concentration.
Figure 3:
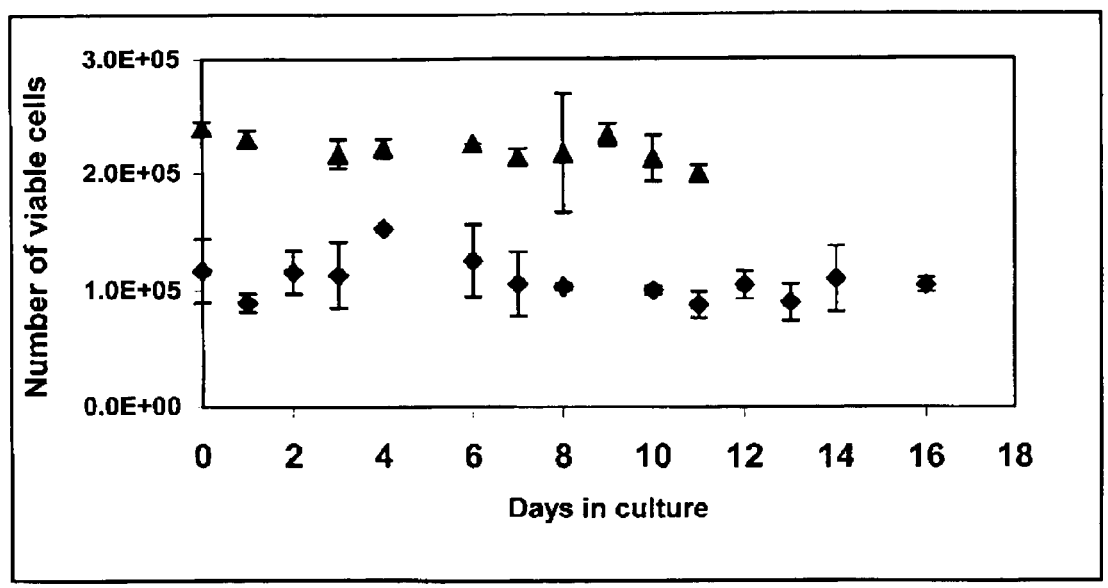
FIG. 3 shows the viability of the seeded cells within the alginate scaffolds as a function of cell seeding concentration; ♦ $10^5$ ▲ $2.5 \times 10^5$ • $5 \times 10^5$ □ $10^6$ cells/scaffold.
Figure 3:
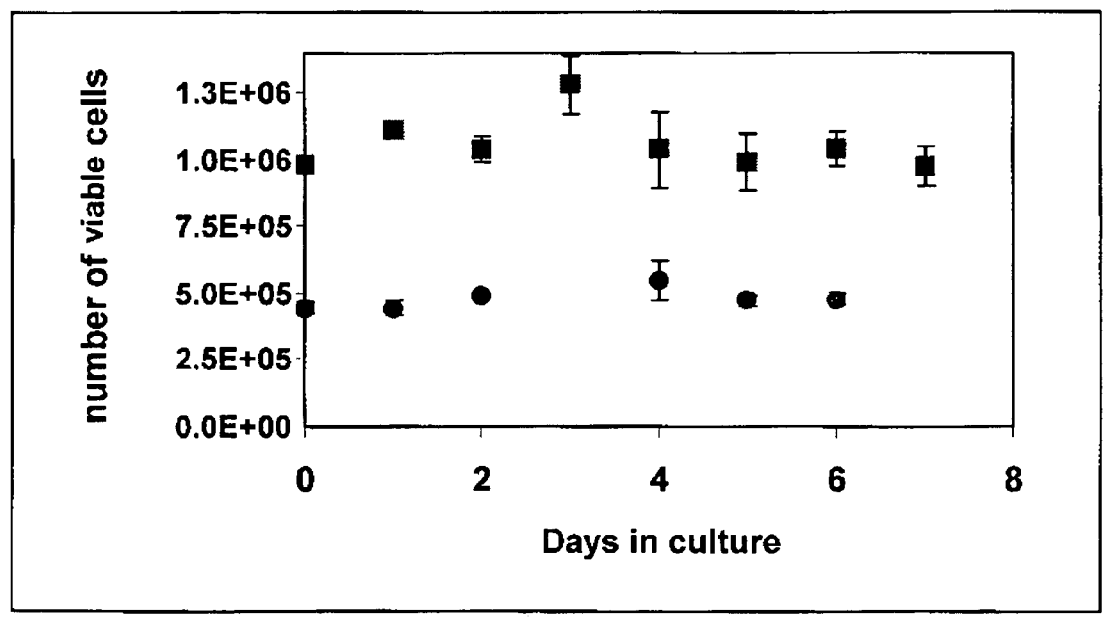

The efficiency of cell loading within the scaffold was characterized within 24 hrs after cell seeding, by determining the total cell number by quantifying the DNA content of a crude cellular homogenate of the cardiomyocytes using the fluorescence enhancement of 4',6-diamidino-2-phenylindole (DAPI) complexed with DNA, as presently known in the art. The number of viable cells in the scaffolds was evaluated using the 3-{4,5-dimethylthiazol-2-yl}-2,5-diphenyltetrazolium bromide (MTT) assay, which measures the ability of mitochondrial dehydrogenase enzymes to convert the soluble yellow MTT salt into insoluble purple formazan salt, as presently known in the art. According to these methods, between 85–90% of the seeded cells were efficiently entrapped within the scaffolds. FIG. 2 shows a photograph of the cell-seeded alginate scaffolds as a function of cell seeding concentration, in the range of $1\times10^5$ cells/scaffold to $2\times10^6$ cells/scaffold. MTT assay was performed on the different seeded scaffolds to verify cell viability and distribution. As seen, the amount of formed purple formazan increased with the increase in cell seeding density. The formazan was distributed in the entire scaffolds. The viability of the seeded cells within alginate scaffolds was maintained for almost a month in culture, according to the MTT viability assay (FIG. 3). It appears that the alginate scaffolds were capable of retaining the cells and no significant cell leakage from the scaffolds was observed.

Figure 4:
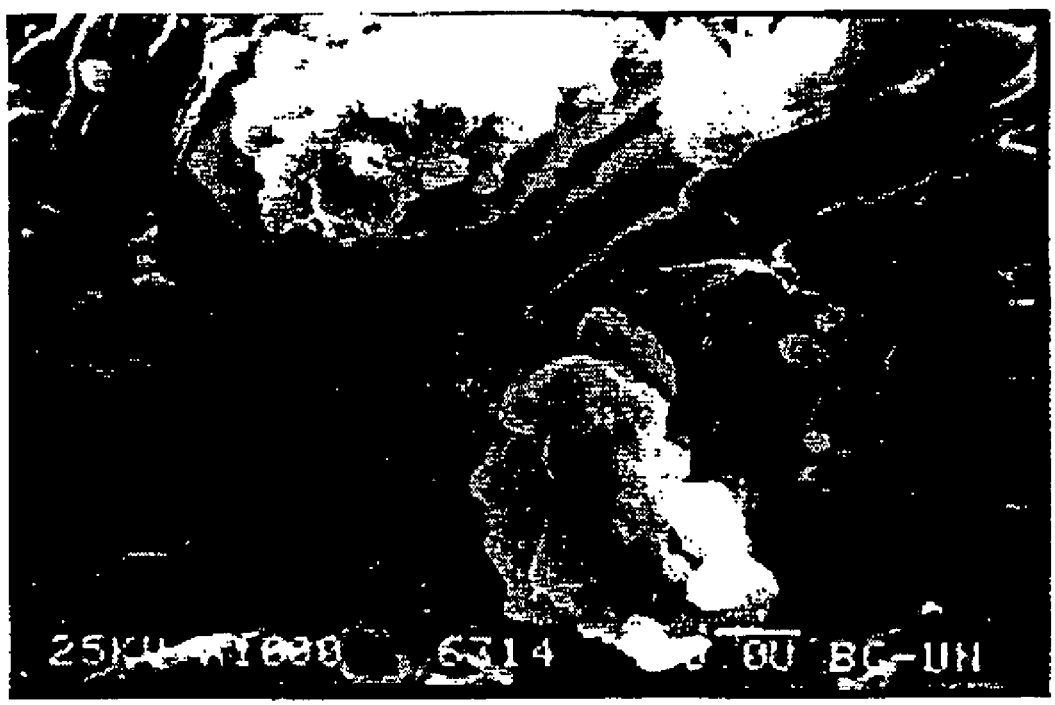
FIG. 4 is a SEM picture of a scaffold cross-section, 4 days after cell seeding within the scaffold.

The morphology of the cells seeded within the 3-D alginate scaffolds was followed by scanning electron microscope (SEM). The cell-seeded scaffolds were washed extensively with PBS, and then fixed in 2.5% (w/v) glutaraldehyde in PBS. After washing with PBS buffer three times, the scaffolds were dehydrated in a graded series of water-ethanol solutions and critical-point dried. Thin sections of the cell-seeded sponges were gold-sputtered (100 A°·thickness) and examined by SEM (model JSM 35 CF, Jeol, Japan) at 25 kV electron beam radiation. FIG. 4 is a SEM picture of a scaffold cross-section, 4 days after cell seeding within the scaffold. As seen, the cells were arranged as multicellular aggregates, which were located within the scaffold pores. By a phase contrast microscope, the cell aggregates were viable and were contracting spontaneously and rhythmically. Thus, it appears that the cells are forming a caridac-like tissue within the alginate scaffolds with time.

Figure 5:
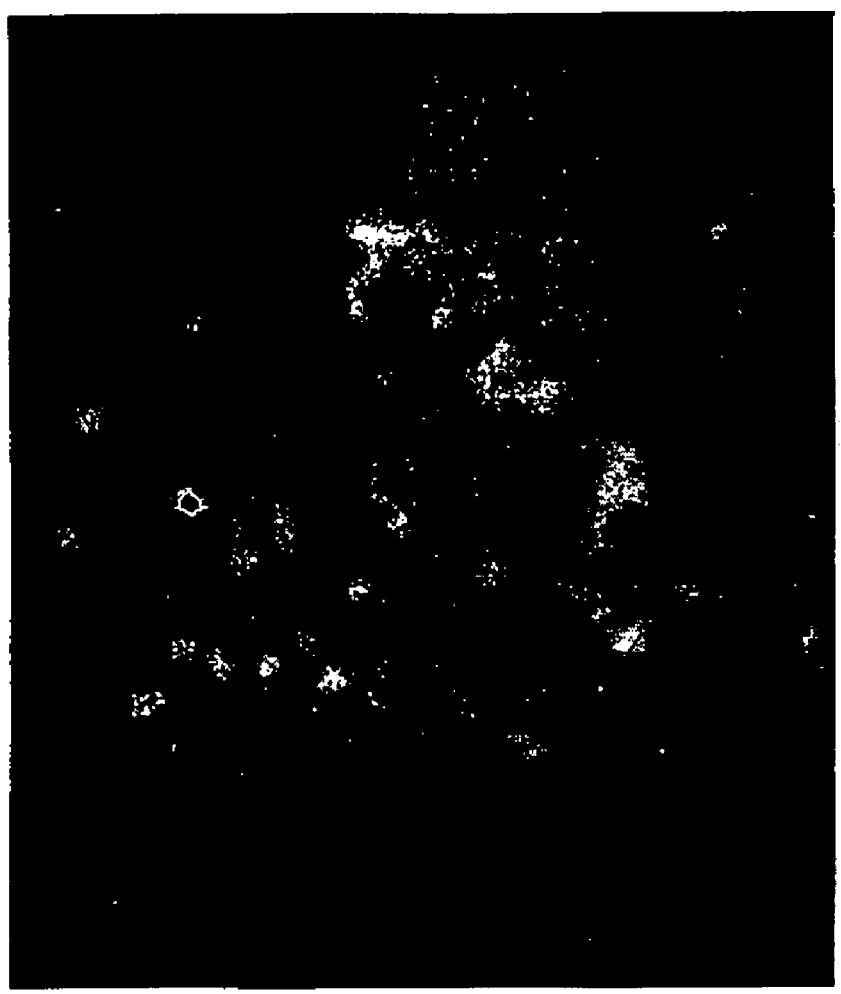
FIG. 5 shows the immunohistochemical analysis for ECM components of the multicellular aggregates within the scaffolds.

In order to further characterize the cardiac biograft, immunohistochemistry was used using antibodies for various components of the extracellular matrix (ECM). Thin-sections of cell-seeded alginate scaffolds were analyzed by an indirect immunofluorescent assay using sheep anti-human fibronectin (Serotec), rabbit anti-mouse laminin (ICN) and rabbit anti-human collagen type I (ICN). The samples were frozen in liquid nitrogen and then processed for cryostat sectioning. Frozen sections (12 μ-thick) were placed on microscope slides and air-dried. They were overlaid with 0.3 ml of the specific antibody diluted at an appropriate concentration and kept for 1 h at 37° C. After washing, the slides were incubated for 1 h in the present of the appropriate FITC-conjugated anti-immunoglobulin antibody diluted 1:200, rinsed, and viewed under an inverted fluorescence microscope (Olympus, Germany) equipped with a 490 nm band-pass filter with a 510-nm cutoff filter for fluorescence emission. FIG. 5 shows the results of the immunohistochemical analysis for ECM components of the multicellular aggregates within the scaffolds, at day 7 postseeding. They were positively stained for fibronectin, laminin and collagen type I. It appears that the ECM was deposited on the surface and between the individual cells that constitute the multicellular aggregates. Control empty scaffolds, or cell-seeded scaffolds reacted only with the second FITC-conjugated antibody, were not stained.

EXAMPLE 2

Figure 6:
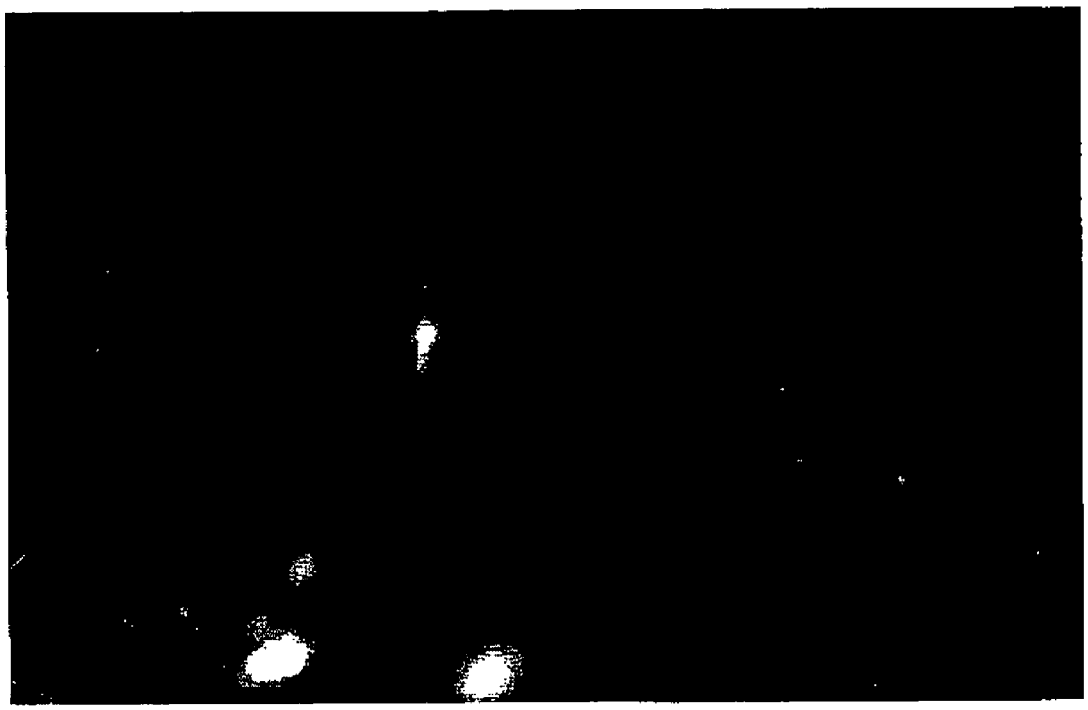
FIG. 6 is a fluorescent micrograph of the seeded endothelial cells organized into a capillary-like structure within the scaffold in-vitro.

Tissue Engineering of Capillary-Like Tubes from Endothelial Cells Seeded within 3-D Alginate Scaffolds, In Vitro Culturing of Endothelial Cells within the 3-D Alginate Scaffolds:

For the isolation of Aortic Endothelial Cells, the aorta was aseptically collected, stripped of adventitia and sliced into rings. The rings were cultured on a tissue flask in an incubator, at 37° C., without medium. After an hour incubation, DMEM supplemented with 10% FBS, 0.02 μg/ml bFGF, 100 U/ml nystatin, 5 μg/ml insulin, 5 μg/ml transferrin, 5 ng/ml sodium selenite and penicillin-streptomycin, was added. The endothelial cells grew as colonies from the aortic rings, and then were expanded as pure population of endothelial cells. Purity of the cells was analyzed by FACS using anti-von Willebrant Factor antibodies. The endothelial cells were seeded onto the alginate scaffolds at an initial cell density of 1 million per scaffold. The growth medium was supplemented with rHuVEGF165 VEGF (50 ng/ml) (produced using baculovirus recombinant system and affinity-purified to yield the native disulfide linked dimer (45 kDa)). The organization and viability of the cells was followed by a fluorescent double staining technique. This technique uses DiOC18, which stains membranes of viable cells in green and Propidium iodide, which stains in red the nuclei of dead cells. Within 2 weeks in culture the seeded endothelial cells were organized into a cord-like structure within the scaffold in vitro (FIG. 6). Nearly all the cells were viable as they were all stained only in green. In addition, the two cords were not on the same plane, indicating the presence of a three-dimensional structure.

Figure 7:
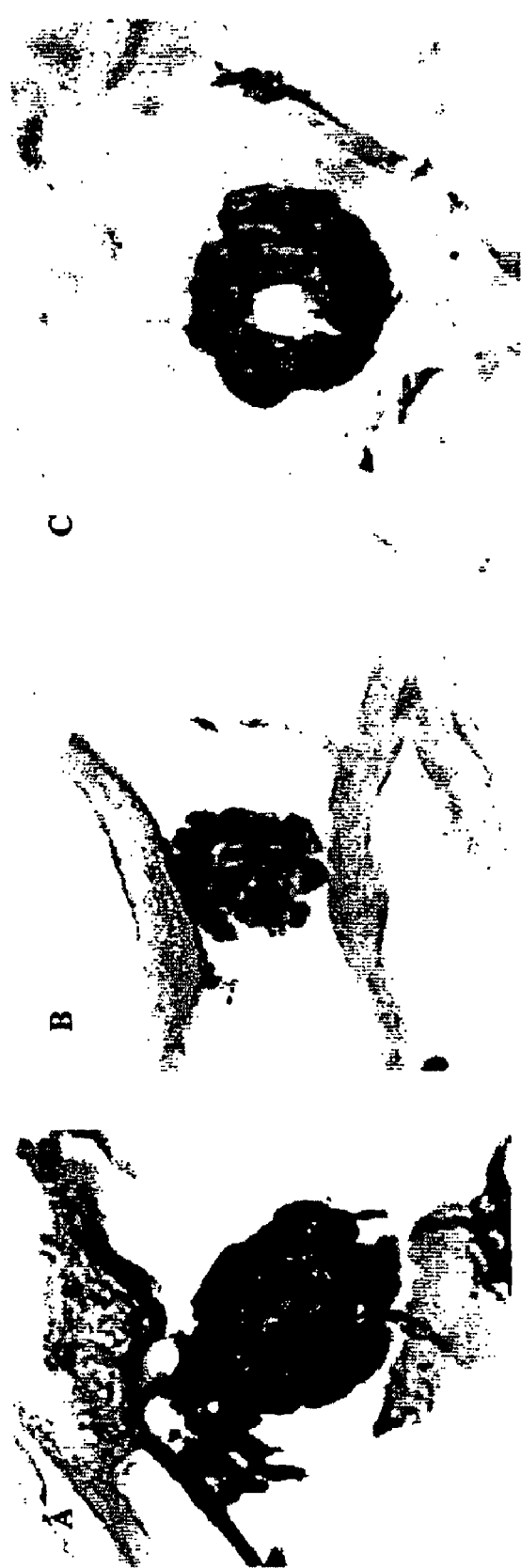
FIGS. 7(A–C) is an histological micrograph showing the process of capillary-like tube formation within the alginate scaffolds. Micrographs taken after 2$d$ (A), 7$d$ (B) and 14$d$ (C)

To verify the existence of a lumen in the cords, a gelatin-paraffin double embedding technique was used. The biografts were fixed in 10% neutral buffered formalin for 30 min, washed three times in DMEM solution and incubated for 1 hr in gelatin solution. The biografts in gelatin were cooled at 40° C. for 5 min, and transferred to 10% neutral buffered formalin for overnight incubation. The biografts were horizontally sliced (3–4 mm thick slices), then placed in a processing cassette and paraffin embedded. 6 μm-thick slices were cut and air dried for 2 days in an incubator at 37° C. The slices were immunostained using rabbit-anti human von willebrand factor (factor VIII)-IgG, which reacts specifically with cytoplasm of endothelial cells. As a counter staining, the cells were stained with hematoxylin. FIG. 7 demonstrates the process of cord formation within the alginate scaffolds. At first, the cells were organized into multicellular aggregates within two days in culture (FIG. 7A). The cell aggregate was positively stained with Anti-factor VIII, indicating that the endothelial nature of cells is maintained. After one week, it was possible to identify further organization of the cells composing the aggregate (FIG. 7B). The endothelial cells at the periphery of the aggregate were organized in a row. Two weeks after the cell seeding the formation of rings could be identified (FIG. 7C). Rings composed from endothelial cells were found in successive serial sections, indicating that the tissue-engineered tubes have a lumen.

EXAMPLE 3

Preparation of Composite Alginate Scaffolds Containing Microspheres with Controlled Release Growth Factors The microspheres containing the growth factors are prepared from poly(D,L-Lactide-(o-glycolide) (PLGA) (RG502H, Boehringer Ingelheim, Germany) by the solvent evaporation method, based on a double emulsion (Cohen et al., Pharmaceutical Research, 8, 713–720, 1991). The polymer was dissolved in a volatile organic solvent, methylene chloride. An aqueous solution containing the growth factors was added to the polymer solution, and the mixture was homogenized to create an inner emulsion. This emulsion was further emulsified in a second aqueous phase that contained a surface active agent such as poly(vinyl alcohol). The resulting double emulsion was stirred until all organic solvent was evaporated, leaving solid microspheres. To formulate the composite scaffold, the microspheres were suspended in the alginate solution, and scaffold preparation proceeds as described in Example 1.

Figure 8:
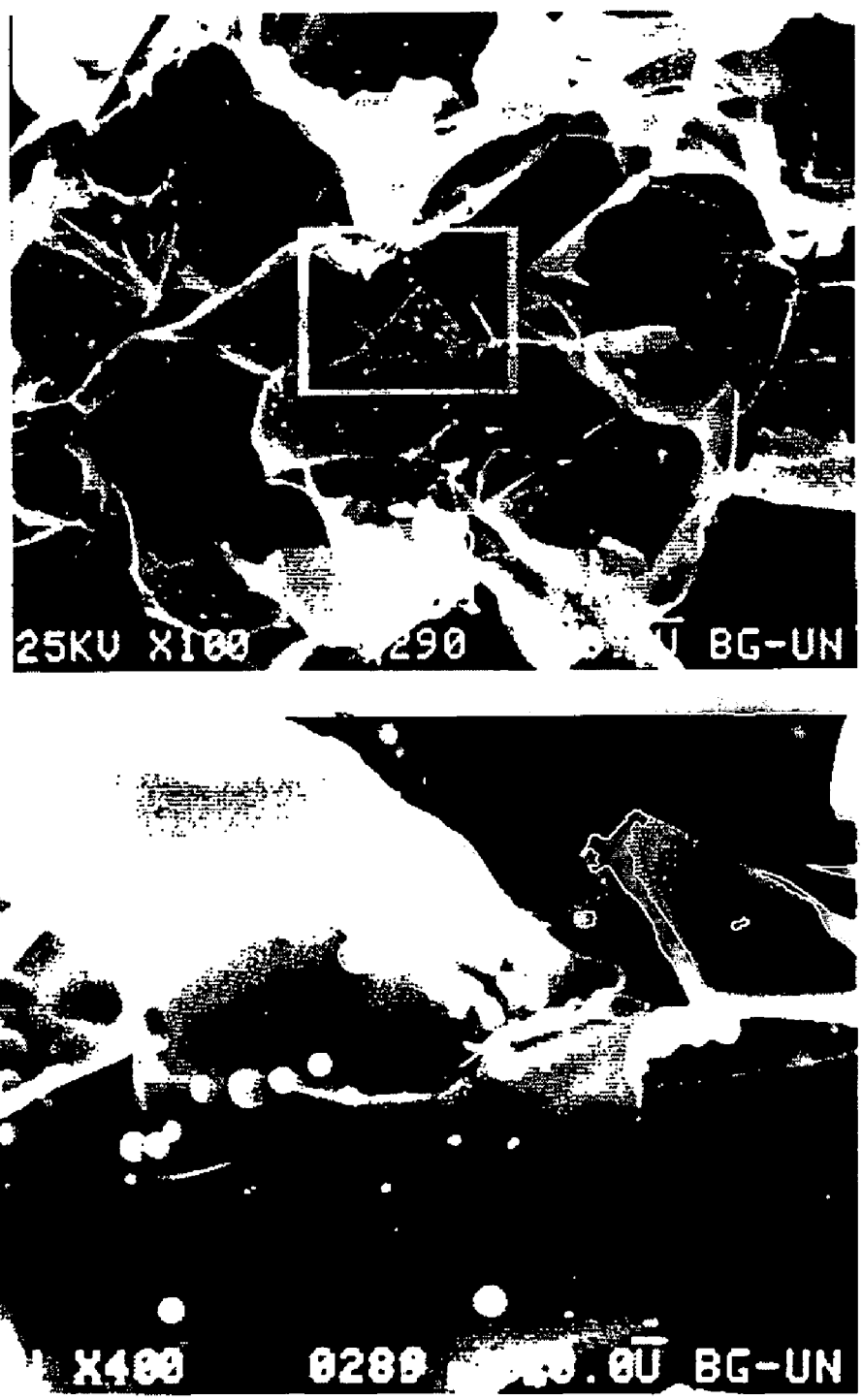
FIG. 8 depicts the SEM morphology of alginate scaffold composites at ×100 (A) and ×400 (B) magnifications.
Figure 9:
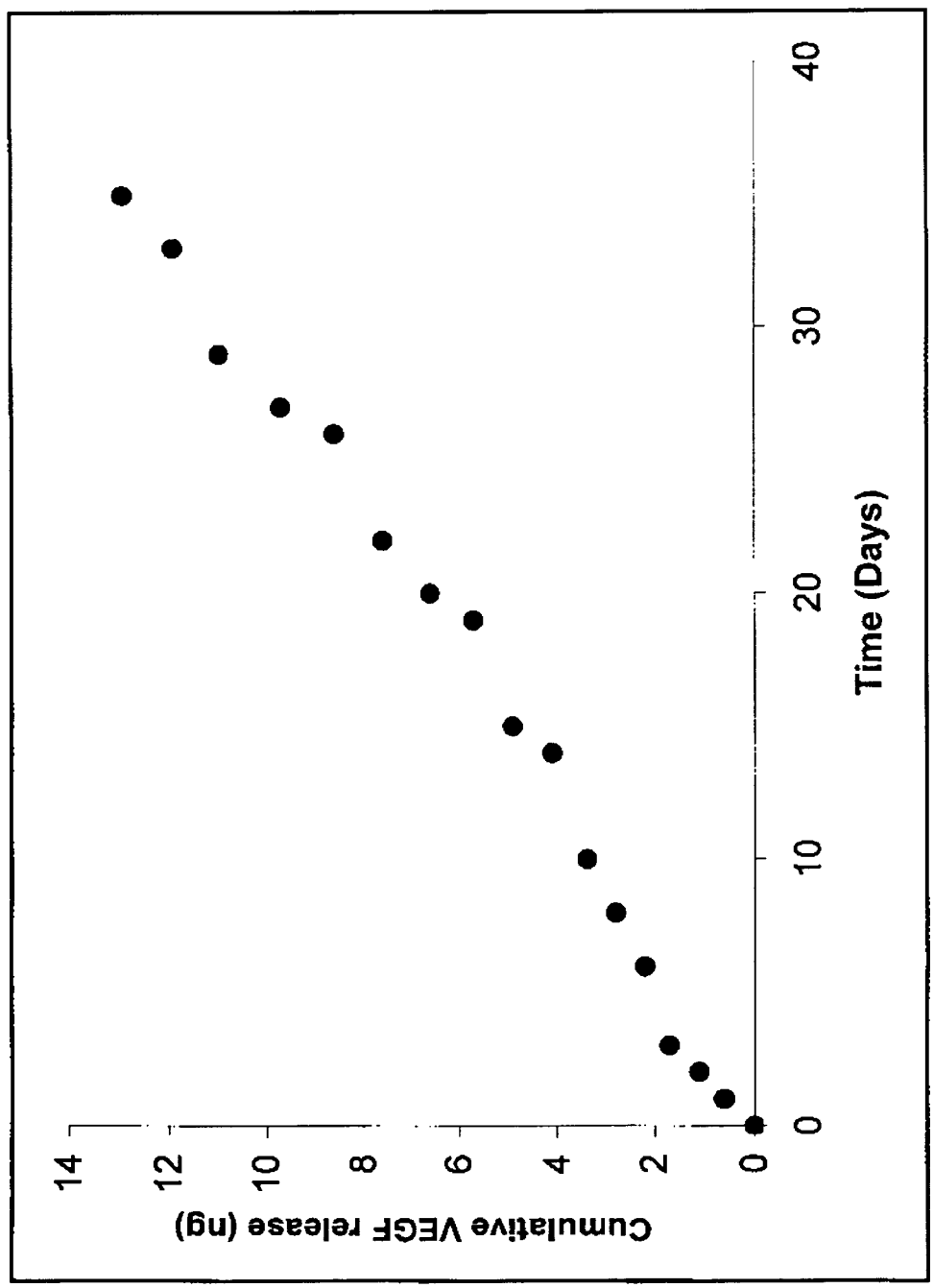
FIG. 9 depicts the release kinetics of VEGF from the composite scaffolds.

The alginate scaffold composites displayed a highly porous structure (>90% porosity), with uniformly distributed pore size of 100 µm. The incorporation of the 5 µm-diameter PLGA microspheres during scaffold preparation did not affect its porous morphology. FIG. 8 depicts the SEM morphology of alginate scaffold composites at different magnifications. The microspheres appeared to be evenly distributed throughout the construct (FIG. 8A). Analysis at higher magnification revealed that the microspheres are in fact an integral part of the scaffold wall (FIG. 8B), and do not interfere with pore structure. FIG. 9 depicts the release characteristics of VEGF from the composite scaffolds. The concentration of VEGF in the medium was determined using an enzyme-linked immuno assay (ELISA). As seen, the release pattern was characterized with a continuous protein release for over a month. When compared to the degradation kinetics of these microspheres, it appears that the microspheres released the growth factors in both diffusion and degradation-dependent manner.

EXAMPLE 4

Biograft Transplantation within the Infarcted Myocardium

Myocardial infarction was induced in female Sprague-Dawley rats by permanent occlusion of the left main coronary artery by an intramural stitch (Leor et al., Circulation, 94 (suppl II): II332–II336, 1996). The experimental group (n=6) was treated with biograft transplantation and the control group (n=6) was treated with sham transplantation (insertion of one suture into the myocardial scar). Biograft transplantation and sham transplantation were performed 7 days after MI. Rats were anesthetized and the chest was opened under sterile conditions. The infarcted area was identified visually by surface scar and wall motion abnormality. Rats were randomized to implantation of biografts or sham transplantation into the infarcted myocardium. Two scaffolds were attached, by one suture for each, to the scar. Air was expelled from the chest and the surgical incision sutured closed.

EXAMPLE 5

Figure 10:
FIG. 10 is a photograph of a rat heart at week 9 after implantation of the biograft. Original magnification ×5.

Intense Neovascularization and Myofiber Formation within the Implanted Biograft, 9 Weeks Post Implantation Visual inspection of the implanted biograft, 65±5 days post implantation (as described in example 4), revealed that the scaffold was covered by a thin connective tissue enriched with blood vessels (FIG. 10). The extensive neovascularization into the biograft emerged from the neighboring coronary network (B). In addition, a coronary branch (C) that supplies the biograft covered it with an extensive network of vessels.

Figure 11:
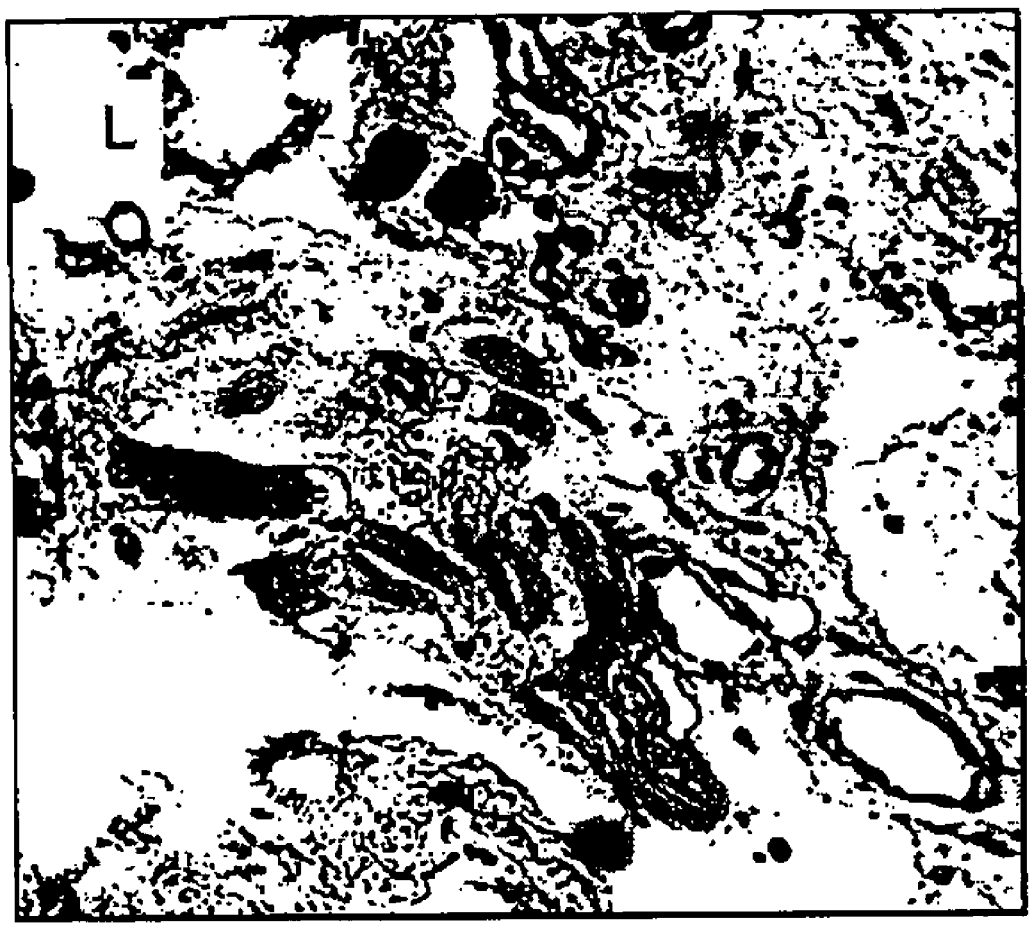
FIG. 11 is high power micrograph of hematoxylin-eosin stained section, of the biograft 9 weeks after implantation. Neovascularization within the biograft is indicated (L). Original magnification ×200.

Adjacent blocks of the harvested heart were embedded in paraffin, sectioned into 5-µm slices and stained for hematoxylin/eosin. Histologic examination of thin sections of the biograft identified differentiated forms of myocardial tissue (FIG. 11). Well-formed myofibers with typical striation were found to grow in between collagen bundles. Some myofibers displayed the normal parallel arrangements of cardiomyocytes, while others were randomly oriented. Significantly, the biografts were populated with newly-formed capillaries and arterioles (L), embedded within the collagen bundle matrix.

EXAMPLE 6

Microscopic Analysis of Biograft Labeled for Connexin 43

Figure 12:
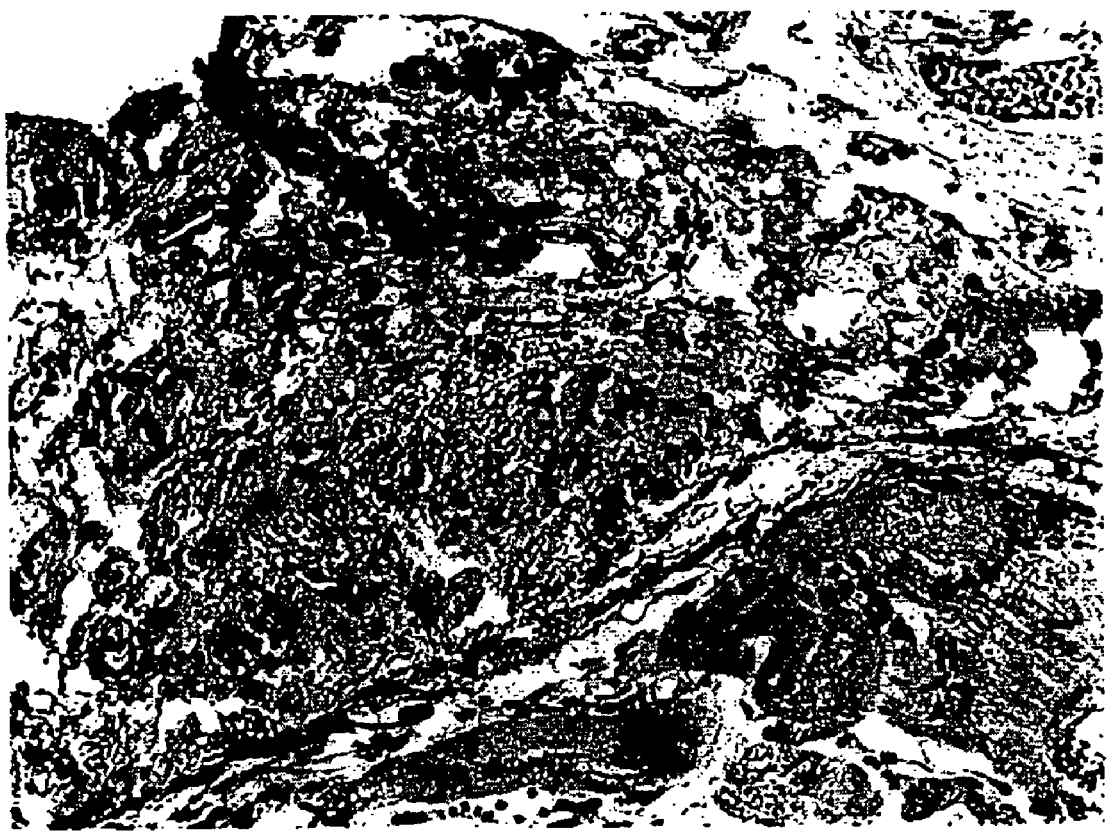
FIG. 12 is a microscopic image of a biograft section labeled for connexin 43, 9 weeks after implantation. Original magnification ×200.

Serial sections of the paraffin embedded tissue blocks (prepared as described in example 5), were immunolabeled with antibodies against the gap junctional protein, connexin 43 (Kanter et al., Circ Res, 72:1124–1131, 1993). Connexin 43 was localized in the normal parallel arrangements in the host myocardium (H in FIG. 12) and randomly oriented in the biograft (B). The presence of cellular gap junctions in these preparations (FIG. 12), indicates the presence of mechanical and electrical connections among the cardiomyocytes in the graft.

EXAMPLE 7

Tissue Ingrowth and Graft Integration with the Host Myocardium

Figure 13:
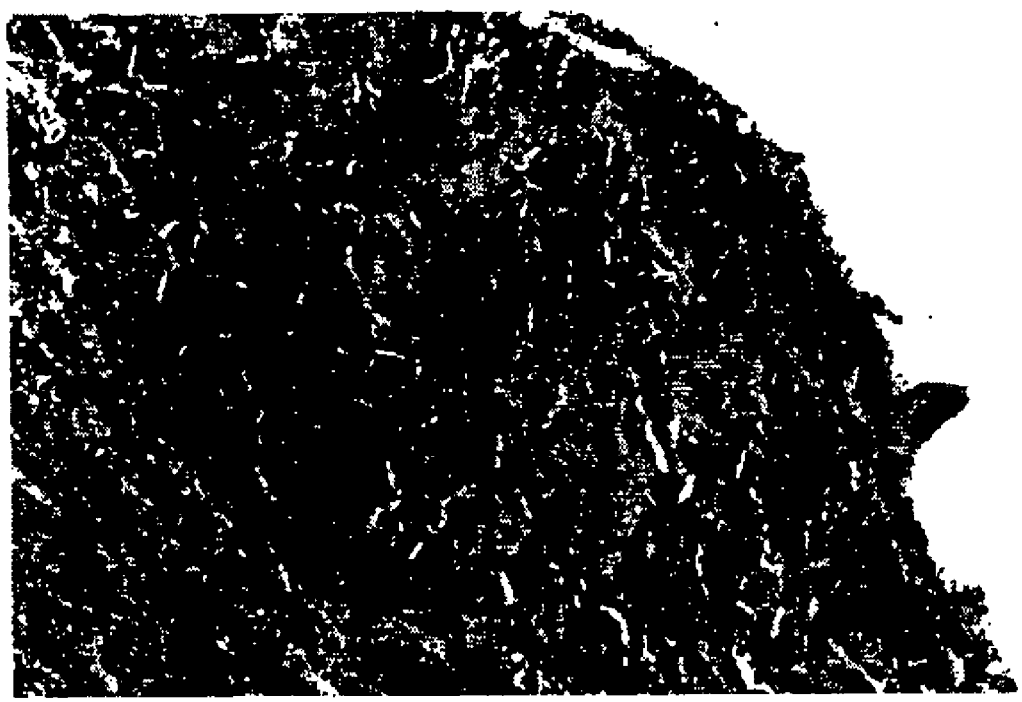
FIG. 13 is a high power micrograph of hematoxylin-eosin stained section, of the biograft 9 weeks after implantation. Original magnification ×100.

Histological staining of thin sections of the biograft, 9 weeks post implantation (prepared from the tissue blocks described in example 5), revealed tissue ingrowth characterized by the presence of fibrous strands of collagen (FIG. 13). At many anchorage sites, the biograft showed integration with the host myocardium (H) and the specimens showed almost complete disappearance of the scaffold.

Figure 14:
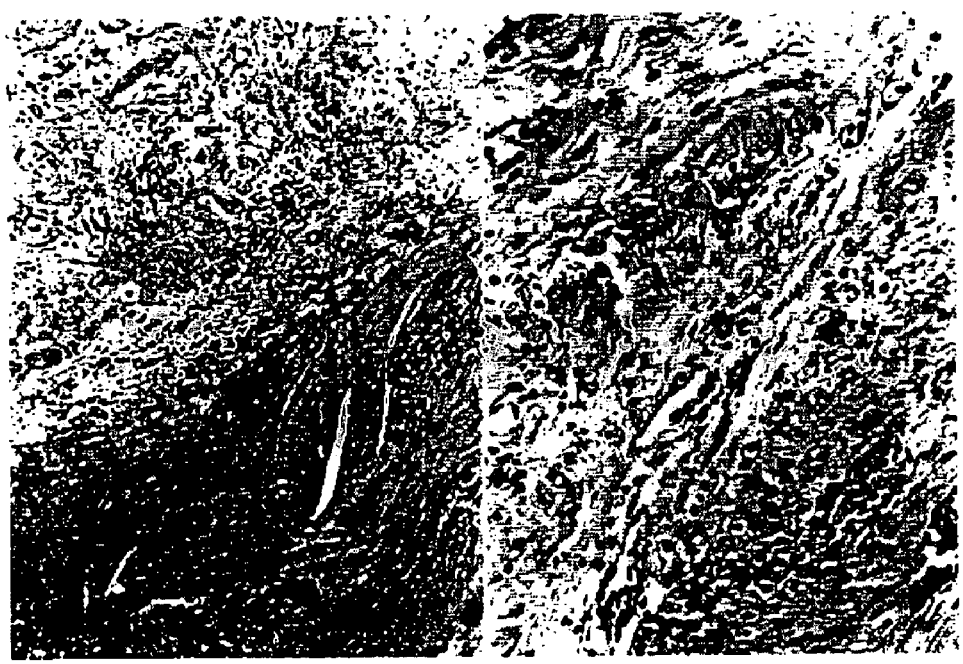
FIG. 14(A+B) is a high power micrograph of hematoxylin-eosin stained section of the biograft based on scaffold composite containing controlled-released VEGF microspheres, 9 weeks after implantation. Original magnification ×100 (A) and ×200 (B).

When tissue-engineered biografts based on the alginate scaffold composites containing VEGF and/or bFGF (see Example 3), were implanted in the infarct scar, the localized release of the growth factors within the scaffold enhanced the vascularization of the scaffold and integration of the biograft into the infarcted myocardium (FIG. 14).

EXAMPLE 8

Echocardiography to Evaluate Remodeling and Contractility

Echocardiography was performed in order to evaluate the influence of the biografts on left ventricular remodeling and function. Transthoracic echocardiography was performed on both experimental and sham animals (treated as described in example 4), 5–7 days after MI, prior to transplantation (baseline echocardiogram), and 65±5 days after transplantation of the biograft (in the experimental group), and after the insertion of the suture (in the sham group). Briefly, rats were anesthetized with ketamine 50 mg/kg and xylasine 10 mg/kg. The chest was shaved, and the rats were placed supine. Echocardiograms were performed with a commercially available echocardiography system equipped with 7.5-MHz phased-array transducer (Hewlett Packered, Andover, Mass.). The transducer was positioned on the left anterior side of the chest after the precordium was shaved. The heart was first imaged in 2-D mode in the parasternal long axis and short axis views of the left ventricle. By the use of these views, the M-mode cursor was positioned perpendicular to the ventricular septum and posterior wall;

M-mode images were then obtained at the level below the tip of the mitral valve leaflets at the level of the papillary muscles. Care was taken to avoid excessive pressure. Posterior wall thickness and LV internal dimensions were measured according to the leading edge method of the American Society of Echocardiography. Maximal LV end-diastolic dimension (at the time of maximal cavity dimension); minimal left ventricular end-systolic dimension (at the time of maximum anterior motion of the posterior wall); and fractional shortening as a measure of systolic function calculated as % FS=[(LVIDd−LVIDs)/LVIDd]×100, where LVID indicates left ventricular internal dimension, s indicates systole, and d indicates diastole. To further validate these measurements and to ascertain the accuracy and reproducibility of the technique, we carried out a reproducibility study in normal rats. All measurements were averaged on three consecutive cardiac cycles and performed by an experienced technician blinded to the treatment group. The statistical significance of differences between measurements before and after transplantation was assessed by use of the paired t test.

The sham group developed a typical course of LV remodeling and heart failure complicating anterior MI. After 3 months, LV end-diastolic and systolic internal diameters increased progressively, by 31% and 65% respectively (Table IA). Progressive LV dilatation was also accompanied by significant deterioration in LV performance, shown by the deterioration of fractional shortening (from 47±2% at baseline to 33±4%; p=0.005) at the end of the study.

Conversely, in the biograft-treated rats, attenuation of all LV remodeling indices was observed (Table IB). During the follow-up period, there was no significant change in the LV internal diastolic and systolic diameters (0.64±0.04 vs. 0.69±0.02 cm; p=0.31, and 0.32±0.04 vs. 0.37±0.04 cm; p=0.52, respectively). The beneficial effect of the biografts on LV remodeling is seen in the prevention of LV function deterioration, as reflected by preservation of fractional shortening after implantation (53±4 vs. 47±5%, p=0.52).

TABLE I

| A. Sham group | | | |
|---|---|---|---|
| | Baseline echocardiogram | 9 wks after suture insertion | P |
| LV internal diameter (cm): | | | |
| End diastole | 0.64 ± 0.03 | 0.84 ± 0.05 | 0.03 |
| End systole | 0.33 ± 0.02 | 0.55 ± 0.06 | 0.02 |
| Fractional shortening (%) | 47 ± 2 | 33 ± 4 | 0.005 |
| LV wall thickness (cm): | | | |
| Anterior | 0.10 ± 0.004 | 0.09 ± 0.01 | 0.34 |
| Posterior | 0.12 ± 0.006 | 0.13 ± 0.002 | 0.07 |
| B. Biograft-treated group | | | |
| | Baseline echocardiogram | 9 wks after biograft transplantation | P |
| LV internal diameter (cm): | | | |
| End diastole | 0.64 ± 0.04 | 0.69 ± 0.02 | 0.32 |
| End systole | 0.32 ± 0.04 | 0.37 ± 0.04 | 0.52 |

TABLE I-continued

| Fractional shortening (%) | 53 ± 4 | 47 ± 5 | 0.52 |
|---|---|---|---|
| LV wall thickness (cm): | | | |
| Anterior | 0.09 ± 0.004 | 0.10 ± 0.007 | 0.21 |
| Posterior | 0.11 ± 0.006 | 0.12 ± 0.007 | 0.44 |

While specific embodiments of the invention have been described for the purpose of illustration, it will be understood that the invention may be carried out in practice by skilled persons with many modifications, variations and adaptations, without departing from its spirit or exceeding the scope of the claims.

The invention claimed is:

1. A method for repairing a damaged myocardium in a mammal, comprising:
    a) providing a three-dimensional porous polysaccharide matrix;
    b) introducing mammalian cells into said matrix;
    c) growing said cells in said matrix in vitro, until a tissue-engineered biograft is formed, comprising a contracting tissue; and
    d) transplanting the tissue-engineered biograft onto myocardial tissue or myocardial scar tissue of said mammal, optionally previously removing scar or dead tissue from the site of implantation;
    wherein the mammalian cells are fetal, autologous, or allogeneic cardiomyocytes, and
    wherein said polysaccharide matrix further comprises controlled-release polymeric microspheres, said microspheres being capable of releasing soluble angiogenic growth factors in a controlled manner.

2. A method according to claim 1, wherein the polysaccharide matrix generates a scaffold.

3. A method according to claim 2, wherein said mammalian cells are combined with at least one of endothelial cells, fibroblasts, or smooth muscle cells that are fetal, autologous, or allogeneic.

4. A method according to claim 3, wherein said endothelial cells form capillary-like tubes within the scaffold.

5. A method according to claim 1, wherein said myocardial damage is due to myocardial infarction.

6. A method according to claim 1, wherein said myocardial damage is due to congenital heart defect.

7. A method according to claim 1, wherein said cardiomyocytes are fetal cardiomyocytes, neonatal cardiomyocytes, or adult cardiac cells.

8. A method according to claim 1, wherein said polysaccharide matrix comprises an alginate polysaccharide.

9. A method according to claim 8, wherein the polysaccharide matrix generates a scaffold.

* * * * *